(12) United States Patent
Hebert et al.

(10) Patent No.: US 10,376,710 B2
(45) Date of Patent: Aug. 13, 2019

(54) APPARATUS AND METHOD FOR INFLUENCING A CONDITION IN A SUBJECT

(71) Applicant: UNIVERSITE LAVAL, Quebec (CA)

(72) Inventors: Marc Hebert, Quebec (CA); Louis Lafleur, Quebec (CA)

(73) Assignee: UNIVERSITÉ LAVAL, Quebec (CA)

( * ) Notice: Subject to any disclaimer, the term of this patent is extended or adjusted under 35 U.S.C. 154(b) by 0 days.

(21) Appl. No.: 15/452,985

(22) Filed: Mar. 8, 2017

(65) Prior Publication Data

US 2017/0173361 A1 Jun. 22, 2017

Related U.S. Application Data

(63) Continuation of application No. 12/733,259, filed as application No. PCT/CA2008/001491 on Aug. 20, 2008.

(60) Provisional application No. 60/935,584, filed on Aug. 20, 2007.

(51) Int. Cl.
*A61N 5/06* (2006.01)
*A61M 21/00* (2006.01)

(52) U.S. Cl.
CPC .......... *A61N 5/0618* (2013.01); *A61M 21/00* (2013.01); *A61M 2021/0044* (2013.01); *A61M 2021/0083* (2013.01); *A61M 2209/088* (2013.01); *A61N 2005/0626* (2013.01); *A61N 2005/0642* (2013.01); *A61N 2005/0648* (2013.01); *A61N 2005/0652* (2013.01); *A61N 2005/0662* (2013.01)

(58) Field of Classification Search
CPC .......... A61B 2018/2075; A61N 5/0618; A61N 2005/0648; A61M 2021/0044; A61M 2021/0083; A61M 2021/0005; A61M 21/00; A61M 21/02
USPC ...................................... 606/2, 3; 607/88, 89
See application file for complete search history.

(56) References Cited

U.S. PATENT DOCUMENTS

| 6,461,019 B1 * | 10/2002 | Allen | F21V 19/001 362/249.06 |
|---|---|---|---|
| 2008/0170476 A1 * | 7/2008 | Hurst | A61M 21/00 368/250 |

OTHER PUBLICATIONS

Technical Datasheet DS05, LemiLEDS-SuperFlux LEDs, Jan. 2005.*
Declaration of Dr. Marc Hébert under 37 C.F.R. § 1.132 dated Jun. 18, 2018.
Exhibit A; Berson et al.; Phototransduction by Retinal Ganglion Cells That Set the Circadian Clock; Date: Feb. 8, 2002; vol. 295, pp. 1070-1073; Science; < www.sciencemag.org>.
(Continued)

*Primary Examiner* — Tod T Van Roy
(74) *Attorney, Agent, or Firm* — Erise IP, P.A.

(57) ABSTRACT

The present invention relates to an artificial light system for modulating circadian rhythms, increasing vigilance and influencing light-associated psychological conditions such as seasonal affective disorder. The system of the invention comprises a source of a green and/or red light and a source of blue light both light sources being controlled by a computer to provide predetermined light conditions. More specifically, the computer is programmed to provide pulses of blue light and continuous or pulsed red light, to enhance the efficacy of blue light, reduce blue-light hazard and avoid stroboscopic effect.

27 Claims, 10 Drawing Sheets

(56) References Cited

OTHER PUBLICATIONS

Exhibit B; Paul et al.; The role of retinal photoreceptors in the regulation of circadian rhythms; Date: Dec. 2009; pp. 1-13; National Institutes of Health.
Exhibit C; Karnas et al.; Intrinsic Photosensitive Retinal Ganglion Cells in the Diurnal Rodent, Arvicanthis ansorgei; Dated: Aug. 9, 2013; pp. 1-16, vol. 8, Issue 8; PLOS ONE; <www.plosone.org>.

* cited by examiner

APPARATUS AND METHOD FOR INFLUENCING A CONDITION IN A SUBJECT

RELATED APPLICATIONS

The present application is a continuation patent application and claims priority benefit, with regard to all common subject matter, of U.S. patent application Ser. No. 12/733,259, filed May 6, 2010, and entitled "ARTIFICIAL LIGHT APPARATUS AND ITS USE FOR INFLUENCING A CONDITION IN A SUBJECT," ("the '259 application"). The '259 application was filed under 35 U.S.C. § 371 and thus, claims priority benefit, with regard to all common subject matter, of International Application No. PCT/CA2008/001491, filed Aug. 20, 2008, and entitled "ARTIFICIAL LIGHT APPARATUS AND ITS USE FOR INFLUENCING A CONDITION IN A SUBJECT" ("the PCT Application"). The PCT Application claims priority benefit of U.S. Provisional Application No. 60/935,584, filed Aug. 20, 2007. The above-referenced applications are herein incorporated by reference in their entirety.

FIELD OF THE INVENTION

The present invention relates to an artificial light system and a method for influencing a condition in a subject. More particularly, this invention relates to a system and a method for influencing circadian rhythms, increasing vigilance and treating psychological conditions that make use of pulsed blue light to enhance the response of a subject's biological clock, minimize blue light hazard and avoid a stroboscopic effect during light exposure.

BACKGROUND OF THE INVENTION

Suprachiasmatic nuclei (SCN) constitute the parts of the hypothalamus that are involved in the control of more than 150 daily biological cycles, including cortisol and melatonin secretion, appetite, body temperature, vigilance and sleep rhythms.

Synchronization of suprachiasmatic nuclei with the 24-hour cycle generated by the earth's rotation is modulated by the alternating exposure to light and darkness. The response of SCN to light conditions is attributable to the presence of light-sensitive receptors in the retina, which signal the SCN accordingly. As natural light conditions vary through each 24-hour period, SCN receive different stimuli and modulate biological rhythms accordingly. As such, SCN were designated colloquially as the "biological clock".

Modulation of the SCN activity and biological rhythms controlled thereby tend to be problematic where a subject's activities are not synchronized with the natural light and dark cycle. One known example relates to night-shift workers, where individuals are mentally and physically solicited while their circadian rhythms advocate for sleep. As such, the desynchronisation of work-related activities and natural light and dark cycle is associated with a decrease in vigilance, a decrease in productivity and an increase of work-related incidents.

Desynchronisation of human activities and natural light conditions can also be observed when traveling by jet airplane across several time zones, a condition best known as "jet lag". While sporadic travellers can adapt to this situation relatively easily after a few days, jet lag may represent a major concern for commercial aircraft crews (e.g. pilots, flight attendants), which do not have the time to adapt and are therefore constantly submitted to circadian rhythms desynchronisation. Further, modulation of SCN activity also appears to influence mood, psychological wellness and light-associated psychological disorders such as, for instance, seasonal affective disorder, a condition also know as winter depression.

Several solutions have been attempted to alleviate problems associated with light-sensitive conditions or with desynchronisation of light cycle and human activities, including the use of artificial light. For instance, U.S. Pat. No. 6,554,439 discloses an apparatus that mimics the intensity and spectrum of natural light and other light dynamic conditions. The apparatus comprises a plurality of light sources of various colours, the light sources being controlled by a computer. The computer modulates the light sources to achieve desired light conditions to mimic natural light conditions (i.e. generally white light) and can be used to modulate circadian cycle and treat psychological disorders.

Similarly, U.S. Pat. No. 6,623,512 discloses a method and an apparatus for modulating circadian cycles or treating a seasonal affective disorder in an individual. The method includes the exposure of the individual's eye to flashes of white light, where each light flash has duration ranging between 1 and 500 milliseconds. According to this method, one light flash per minute is emitted and the individual is subjected to light treatment between 5 and 180 minutes. Because the individual can perceive the alternation of light flashes and light interruptions, refer to as the stroboscopic effect, the method taught in the U.S. Pat. No. 6,623,512 may lead to discomfort, especially when the subject is exposed to such light conditions for an extended period of time.

Further, because the methods and apparatuses taught in both previous patents make use of a generally white light (i.e. a blend of all colors in the spectrum of visible light), their efficiency tends to be reduced. It was indeed reported that the rods and cones (i.e. the classical photoreceptors capable of sensing the visible light spectrum) would not be essential to the transmission of light stimuli to the SCN, this function being rather accomplished by the recently discovered melanopsins, photoreceptors found in less than 1% of the total ganglion cell population.

Contrarily to rods and cones, sensitivity of melanopsins would be confined to a light spectrum in which wavelengths range from 420 to 540 nm, with a sensitivity or wavelength peak between 446 and 483 mm. This wavelength range encompasses the lights that are generally perceived as being blue (wavelength peak at about 470 nm) and green (wavelength peak at 525 nm). Blue light has been shown to be more efficient than white light with respect to the biological impact on performance, vigilance and general resynchronization of the biological clock. As such, use of a light consisting in a broader range of wavelengths, as disclosed in U.S. Pat. Nos. 6,554,439 and 6,623,512, tends to be purposeless and may ultimately lead to energy cost increases.

However, the use of blue light to modulate SCN response is not without limitation. For example, melanopsin photoreceptors tend to degrade fast and not to regenerate upon continuous exposure to blue light, which contribute to reduce the efficacy of blue light upon such sustained exposure.

But more importantly, blue light has been shown to be toxic for retina and to increase the risks of macular diseases, which side effects are commonly referred to as "blue light hazard". Specifically, blue light is absorbed by lipofuscin, which in turns triggers the production of free radicals.

Because the effects of blue light tend to be cumulative over the entire life of the subjects, it may cause irreversible damage.

It would therefore be profitable to be provided with a system that makes use of light for modulating a circadian rhythm, a vigilance state or a psychological condition, where the system allows overcoming the drawbacks generally associated with such use of light.

SUMMARY OF THE INVENTION

In order to address the above and other drawbacks, and in accordance with the present invention, there is disclosed an artificial light system for modulating at least one of a circadian rhythm and a psychological condition in a subject.

According to one embodiment of the present invention, an artificial light system for modulating a condition in a subject is provided. The system comprises a first light-emitting source for emitting a first light having a wavelength spectrum below 540 nm, and a controller. The controller is operatively connected to the first light-emitting source and is programmed to control the first light-emitting source to provide pulses of the first light, wherein the pulses of the first light have a frequency adapted to avoid a stroboscopic effect.

In one feature, the system also comprises a second light-emitting source for emitting a second light having a wavelength spectrum of at least 540 nm.

In another feature, the controller is operatively connected to the second light-emitting source. The controller is programmed to control the first and second light-emitting sources independently.

In yet another feature, the frequency of the light pulses of the first light ranges from about 10 Hz to about 10 kHz, and more preferably from about 10 Hz to about 200 Hz, and even more preferably from about 50 Hz to about 100 Hz.

In one feature, the second light-emitting source is controlled to provide a continuous second light. In an alternate feature, the second light-emitting source is controlled to provide pulses of the second light. According to this feature, the light pulses of the second light have a frequency adapted to avoid a stroboscopic effect. The frequency of light pulses of the second light preferably ranges from about 10 Hz to about 10 kHz, and more preferably from about 10 Hz to about 200 Hz, and even more preferably from about 50 Hz to about 100 Hz.

According to a further feature, the first and second light-emitting sources are controlled to provide pulses of the first and second lights. The light pulses of the first and second light-emitting sources are desynchronized. Preferably, when one of the first and second light-emitting sources is turned on, the other of the first and second light-emitting source is turned off.

According to yet a further feature, the first light has a wavelength spectrum ranging from about 450 nm to about 490 nm. The first light preferably comprises a blue light having a wavelength peak between 460 nm and 484 nm, and more preferably a blue light having a wavelength peak of about 470 nm.

In another feature, the second light has a wavelength spectrum ranging from about 590 nm to about 650 nm. The second light preferably comprises a red light having a wavelength peak between 612 nm and 640 nm, and more preferably a red light having wavelength peak of about 625 nm.

In yet another feature, the system also comprises a third light-emitting source. The third light source emits a third light having a wavelength below 540 nm. Preferably, the third light has a wavelength spectrum ranging from about 490 to about 539 nm. The third light comprises more preferably a green light having a wavelength peak ranging between 510 and 530 nm, and even more preferably a green light having a wavelength peak of about 525 nm.

In a further feature, the condition in the subject is selected from a circadian rhythm, a vigilance state and a psychological condition. Preferably, the circadian rhythm is selected from a group consisting of: hormone secretion, body temperature and sleep rhythm, where hormone secretion comprises at least one of melatonin secretion and cortisol secretion. In an alternate feature, the psychological condition comprises at least one of a seasonal affective disorder, a psychological state of wellness and a mood.

In still a further feature, the light-emitting sources are selected from a group consisting of: a light-emitting diode (LED), a fluorescent tube, an incandescent bulb and a laser.

In yet a further feature, the controller is selected from a group consisting of: a programmable interface controller (PIC), a dedicated circuit, a field-programmable gate array (FPGA), a digital signal processor (DSP) and a computer. The computer is preferably selected from a group consisting of: a desktop computer, a laptop computer, a handheld computer and a personal digital assistant.

In accordance with another embodiment of the present invention, there is provided an artificial light system including a first light-emitting source for emitting a first light having a wavelength below 540 nm and a second light-emitting source for emitting a second light having a wavelength of at least 540 nm. The system further comprises a controller electrically connected to the first and second light-emitting sources. The controller is operable to control the first and second light-emitting sources independently, to provide pulses of the first light and the second light-emitting source to provide the second light. The light pulses of the first light-emitting source have a frequency adapted to avoid a stroboscopic effect.

According to one feature, the pulses of the first light have a frequency adapted to avoid a stroboscopic effect. The frequency of the light pulses of the first light preferably ranges from about 10 Hz to about 10 kHz, and more preferably from about 10 Hz to about 200 Hz, and even more preferably from about 50 Hz to about 100 Hz.

In another feature, the second light-emitting source is controlled to provide a continuous second light. In an alternate feature, the second light-emitting source is controlled to provide pulses of the second light, where the light pulses of the second light preferably have a frequency adapted to avoid a stroboscopic effect. According to this feature, the frequency of light pulses of the second light preferably ranges from about 10 Hz to about 10 kHz, and more preferably from about 10 Hz to about 200 Hz, and even more preferably from about 50 Hz to about 100 Hz.

In a further feature, the first and second light-emitting sources are controlled to provide pulses of the first and second lights, where the light pulses of the first and second light-emitting sources are desynchronized. Preferably, when one of the first and second light-emitting sources is turned on, the other of the first and second light-emitting source is turned off.

In yet a further feature, the first light has a wavelength spectrum ranging from about 450 nm to about 490 nm. The first light is preferably a blue light having a wavelength peak between 460 nm and 484 nm, and more preferably a blue light having a wavelength peak of about 470 nm. The second light has a wavelength spectrum ranging from about 590 nm to about 650 nm, and is preferably a red light having a wavelength peak between 612 nm and 640 nm, and more preferably a red light having wavelength peak of about 625 nm.

In another feature, the system comprises a third light-emitting source. The third The third light-emitting source emits a third light having a wavelength below 540 nm. Preferably, the third light has a wavelength spectrum ranging from about 490 to about 539 nm, and is more preferably a green light having a wavelength peak ranging between 510 and 530 nm, and even more preferably a green light has a wavelength peak of about 525 nm.

In yet another feature, the condition of the subject is selected from a circadian rhythm, a vigilance state and a psychological condition. Preferably, the circadian rhythm is selected from a group consisting of: hormone secretion, body temperature and sleep rhythm, where hormone secretion can be melatonin secretion or cortisol secretion. In a further feature, the psychological condition is a seasonal affective disorder, a psychological wellness or a mood.

In still a further feature, the light-emitting sources are selected from a group consisting of: a light-emitting diode (LED), a fluorescent tube, an incandescent bulb and a laser.

In one feature, the controller is selected from a group consisting of: a programmable interface controller (PIC), a dedicated circuit, a field-programmable gate array (FPGA), a digital signal processor (DSP) and a computer. The computer is preferably selected from a group consisting of: a desktop computer, a laptop computer, a handheld computer and a personal digital assistant.

According to an alternate embodiment of the present invention, a method for modulating a condition in a subject is provided. The method comprises exposing the subject to a first light having a wavelength below 540 nm for a predetermined period of time, where the first light is pulsed so as to avoid a stroboscopic effect thereof and exposing the subject to a second light having a wavelength of at least 540 nm for the predetermined period of time.

In one feature, the second light is pulsed so as to avoid a stroboscopic effect thereof. Preferably, the light pulses of the first and second light-emitting sources are desynchronized, and more preferably, when one of the first and second light-emitting sources is turned on, the other of the first and second light-emitting source is turned off.

In another feature, the frequency of light pulses of the first and second lights ranges from about 10 Hz to about 10 kHz, and preferably ranges from about 10 Hz to about 200 Hz and more preferably ranges from about 50 Hz to about 100 Hz.

In yet another feature, the predetermined period ranges from about 5 minutes to about 18 hours, preferably from about 1 hour to about 8 hours and more preferably from about 3 hours to about 5 hours.

In a further feature, the subject comprises an animal subject, where the animal subject is preferably a human subject. The human subject is preferably selected from a group consisting of: a transport means operator, a night-shift worker and a social establishment customer, where the social establishment customer is more preferably a casino customer.

According to a further embodiment of the present invention, there is provided the use of an artificial light system to modulate a condition in a subject. The system used to modulate such condition comprises a first light-emitting source for emitting a first light having a wavelength below 540 nm and a second light-emitting source for emitting a second light having a wavelength of at least 540 nm. The system also comprises a controller electrically connected to the first and second light-emitting sources and controlling the same independently. The controller is programmed to control the first light-emitting source to provide pulses of the first light and the second light-emitting source to provide the second light.

Other objects, advantages and features of the present invention will become more apparent upon reading of the following non-restrictive description of illustrative embodiments thereof, given by way of example only with reference to the accompanying drawings.

BRIEF DESCRIPTION OF THE DRAWINGS

Having thus generally described the nature of the invention, reference will now be made to the accompanying drawings, showing by way of illustration an illustrative embodiment thereof, and in which.

DESCRIPTION OF THE ILLUSTRATIVE EMBODIMENTS

Figure 1:
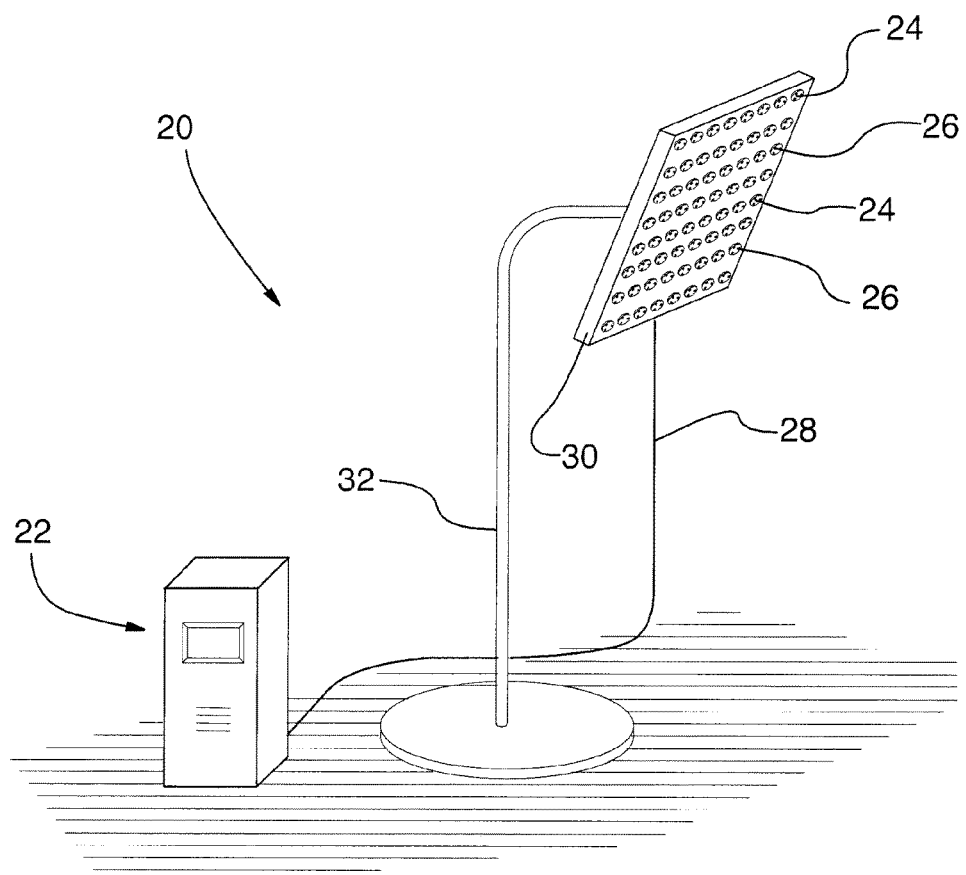
FIG. 1 is a schematic representation of an artificial light system according to one embodiment of the present invention.

The description which follows, and the embodiments described therein are provided by way of illustration of an example, or examples of particular embodiments of principles and aspects of the present invention. These examples are provided for the purpose of explanation and not of limitation, of those principles of the invention. In the description that follows, like parts are marked throughout the specification and the drawings with the same respective reference numerals.

With reference to FIG. 1, a light system identified by reference numeral 20 is provided. The light system 20 is operable to modulate circadian rhythms, vigilance, mood or psychological disorders associated with light conditions such as, for instance, seasonal affective disorder. In one embodiment, the system 20 is used to modulate secretion of melatonin. Melatonin is a hormone secreted by the pineal gland, a gland under the control of SCN. Melatonin is secreted by such gland mainly when light conditions are low, for instance, during the night, and maximum melatonin secretion is generally reached between 2 am and 4 am. Because melatonin has a mild sleepiness-inducing effect, its secretion is generally associated with a decrease in productivity of night-shift workers and an increase of work-related accidents, which both have a financial impact on industries.

When the melanopsins of the retina are exposed to light, SCN react by inducing pineal gland to stop melatonin secretion. It is further known in the art that inhibition of melatonin secretion is dependant upon the efficacy of the response of SCN to light stimulus. In other words, inhibition of melatonin secretion will be stronger in the presence of a strong response of SCN to a light stimulus while inhibition of melatonin secretion is expected to be weaker in the presence of a weak response of SCN to a light stimulus. Such a response of the SCN is known to be influenced, for instance, by age and by the nature of the light stimulus (e.g. wavelength, duration and intensity of light). SCN response is also known to influence body temperature. More specifically, body temperature can vary from up to 1 Celsius degree or 2 Fahrenheit degrees over the course of the day, being lowest around 4:00 to 5:00 a.m. and higher during awakening. As such, body temperature has been used as a marker for monitoring SCN response to different stimuli, including light conditions.

Still referring to FIG. 1, the system 20 comprises a first light source 24 and an electronic light controller 22 electrically connected to an electricity source (not shown) and to the first light source 24 with an electrical wire 28. The controller 22 is operable to control the first light source 24, as best described below.

According to this embodiment the first light-emitting source 24 provides a first light having a wavelength spectrum below 540 nm, and preferably a light having a wavelength spectrum ranging from about 430 nm to about 510 nm and more preferably a blue light, i.e. a light having a wavelength peak between 460 nm and 484 nm, and even more preferably a blue light having a wavelength peak of about 470 nm. The first light source 24 is therefore designated the blue light source for the purpose of the description. A person skilled in the relevant art will understand that this designation is not restricted to a light having a wavelength peak between 460 nm and 484 nm but rather to any light having a wavelength spectra below 540 nm, which is generally referred to as "blue" light.

The first or blue light source 24 may comprise, for instance, one or multiple of LEDs within the above-described wavelength ranges. Alternatively, the first or blue light source can be provided with fluorescent tubes or incandescent bulbs of appropriate colours, or a combination of a white light sources and an appropriate light filter. A person skilled in the art will acknowledge that any source capable of providing a light within the above ranges and capable of being pulsed could be used for the purpose of the present invention.

In the example provided in FIG. 1, the light source 24 is mounted to a generally rectangular frame 30 supported on a movable base 32. Alternatively, the system 20 could be adapted to be permanently incorporated to a building structure such as a wall or a ceiling of a factory, an office, a house, a hospital, a retirement center or the like. In such an embodiment, the light source 24 and the controller 22 can be positioned relatively remote from one another. A person skilled in the art will appreciate that a single controller 22 can be used to control light source 24 found in a plurality of different locations. For instance, a plurality of workstations can be provided with the light source 24, the light conditions of each station being controlled by a same controller 22. Alternatively, independent controllers could modulate the light conditions of each station.

In one embodiment, the controller 22 is adapted to control the parameters of the light emitted by the light source 24, such as, for example, the duration of the light treatment or exposure, the frequency of pulse cycles, the duration of light emission and light interruption within each cycle and the intensity of light. The controller 22 can therefore be a processor or a computer, and comprises a desktop computer, a laptop computer and a handheld computer such as, for instance, a Palm™ personal digital assistant. While a computer may be used, it will be appreciated by a person skilled in the art that other types of controller may be used. For instance, the controller may be a programmable interface controller (PIC), a dedicated circuit, a field-programmable gate array (FPGA), a digital signal processor (DSP) or any other type of controllers.

According to one embodiment of the present invention, the first light source 24 is pulsed so as to avoid stroboscopic effect. Stroboscopic effect can be observed when the duration of light interruption between each light pulse is sufficient to be perceived by an individual or, in other words, the perception by the subject of the on/off cycles of the light. The perception of light (i.e. the vision) is modulated by rods and cones, which signal the brain accordingly. Upon interruption of light for very short periods of time (e.g. within the millisecond (ms) range), the brain tends to virtually fill the gap between two light emissions and interpret the light as being continuous, a phenomenon commonly designated as "image persistence". However, other chemical reactions modulated by light (e.g. light toxicity) are known to be much more responsive to light stimuli than vision.

The present invention therefore takes advantage of the difference in response to light stimuli observed between vision and other chemical reactions, to avoid a stroboscopic effect of the light while reducing the risks of toxicity associated to blue light. Accordingly, in this embodiment, the first light source 24 is controlled by the controller 22 to provide a pulsed light, where the frequency of the pulses ranges from about 10 to about 10,000 cycles per second (i.e. from about 10 Hz to about 10 kHz). For instance, at a frequency of 60 Hz, the total duration of a cycle corresponds to 16.66 ms or approximately 17 ms. Within such a cycle, the first light source 24 is turned on (i.e. the blue light is emitted) for duration of approximately 4 ms and turned off (i.e. no light is emitted) for duration of approximately 13 ms. Despite this embodiment being preferred, the frequency of cycles can be modified without departing from the scope of the invention.

Further, the duration of light emission/interruption within a cycle can be modified. For instance the duration of light emission within a 60 Hz cycle (17 ms) can vary between approximately 1 ms and 10 ms while the light interruption can vary complementarily between approximately 7 and 16 ms. In another exemplary situation, 70 Hz (14 ms) cycles could be selected where the light emission within such a cycle could have a duration ranging between 1 and 10 ms while light interruption would have a complementary duration of approximately 4 to 13 ms. Under such conditions, the stroboscopic effect of light cycles remains unperceivable by a human eye.

The system 20 may also comprise a second light source 26. The second light source 26 is preferably a source of light that provides a second light having a wavelength spectrum of at least 540 nm. In one embodiment, the second light source 26 provides a light having a wavelength spectrum ranging from about 590 nm to about 650 nm, and more preferably a red light, i.e. a light having a wavelength peak between 612 nm and 640 nm, and even more preferably a red light having a wavelength peak of about 625 nm. Similarly to first light source 24, the second light source 26 can comprise a plurality of red LEDs. Alternatively, light source 26 can be provided with red fluorescent tubes or incandescent bulbs, or any source of white light to which a filter is applied to obtain a light within the desired wavelength range.

In one embodiment, the controller 22 is adapted to control the second light source 26 (i.e. the red source) to provide a continuous beam or emission of light while simultaneously controlling first light source 24 to provide a pulsed blue light. In an alternate embodiment, both light sources 24, 26 could be controlled by controller 22 so as to be independently pulsed. In such an embodiment the light cycles of the first or blue light source 24 and second light source 26 are preferably desynchronized. More specifically, the light cycle of the red light source 26 is opposite or complementary to the light cycle of the blue light source 24. In other words, both sources 24, 26 can have a same light cycle (e.g. 60 Hz or approximately 17 ms) but being pulsed at different times. For instance, the blue light may be emitted for a duration of 4 ms and interrupted for 13 ms. Within the same cycle, the red light source 26 is turned off when the blue light is on (i.e. for a duration of 4 ms) and emitted when the blue light source is off (i.e. for a duration of 13 ms). A person skilled in the art will therefore acknowledge that any combination of continuous and/or pulsed light emitted from the second source 26 (i.e. the red light), in conjunction with a blue light pulsed in accordance with the present description, would fulfill the purpose of the invention.

In a further embodiment, the frequency of light cycle and the duration of emission/interruption within a cycle can remain unchanged during the period of light exposure or controlled by controller 22 so as to be modified through the total light exposure period. For instance, at the beginning of a 2-hour light exposure period (e.g. T=0), the frequency of light cycles could be of 70 Hz (14 ms), in which cycle the duration the blue light could be on for 4 ms and further turned off for 10 ms, and where the red light is continuously on. After application of these light conditions for a predetermined period of time (e.g. at T=1 hour), the parameters could be modified to light cycles of 60 Hz (17 ms) in which blue light is on for 1 ms and off for 16 ms and, and the red light pulsed complementarily (i.e. off for 1 ms and on for 16 ms).

The controller 22 is also aimed to control the total duration of the exposure or treatment to light. In one embodiment, the controller 22 is set to automatically provide light treatment for a duration ranging between 15 minutes and 8 hours. The controller could also be set to automatically start light treatment at a predetermined period of the day (e.g. at midnight everyday) or to be manually operated (e.g. when a worker is present at his work station). Despite the application of light treatment can be continuous over a predetermined period, the controller 22 could also be programmed to provide multiple light exposure episodes within such a predetermined period. For instance, the controller 22 could be programmed to provide an individual with a light treatment over a total period of 3 hours, where light cycles would only be applied for a 30-minute episode every hour.

In addition to controlling the length of exposure to light treatment, the frequency of light cycles and duration of light pulse/interruption with a cycle, the controller can be programmed to modulate the intensity of light. In one embodiment, the intensity of light is controlled so as to range from about 5 $\mu W/cm^2$ to about 100 $\mu W/cm^2$. Again, the intensity of light can remain invariable or be modified during the light treatment.

As it will be appreciated by a person skilled in the art, the blended color of the combined blue and red lights emitted by the first and second light sources 24, 26 will tend to be perceived as being purple or lavender, based on the ratio of the red and blue lights. As the use of red and blue light sources cannot provide a generally white light and because a generally purple light may not be ideal in every occasions (e.g. at a work station), it may be desirable to add further light sources to provide a blended light having the appearance of a white light, without compromising the efficacy of the system 20. As such, the system may comprise a third light source (not shown) for providing a third light. According to this embodiment, the third light has a wavelength below 540 nm, and is preferably a green light, i.e. a light having a wavelength peak ranging from about 490 nm to about 539 nm, and more preferably a green light having a wavelength peak of about 525 nm. In this exemplary situation, the third or green light could be could be pulsed in synchrony with the blue light and collaborate therewith to activate melanopsins.

Figure 3:
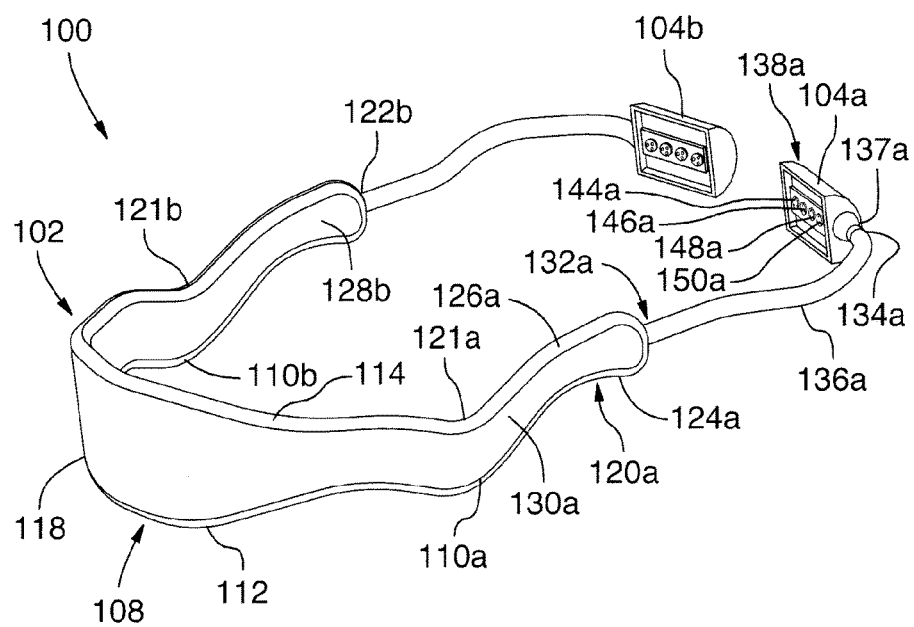
FIG. 3 is a back right perspective view of the artificial light system shown in FIG. 2.
Figure 4:
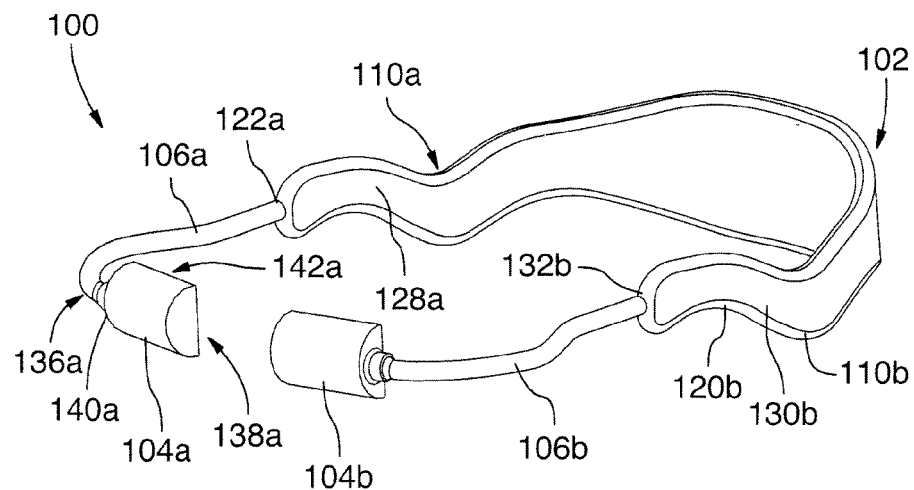
FIG. 4 is a front left perspective view of the artificial light system shown in FIG. 2.

A person skilled in the art will further appreciate that the physical configuration (e.g. forms, shape) of the light system is not critical to the function. For instance, FIGS. 2 to 4 show a portable light system according to an alternate embodiment, which portable system is generally designated using the reference manual 100.

Figure 2:
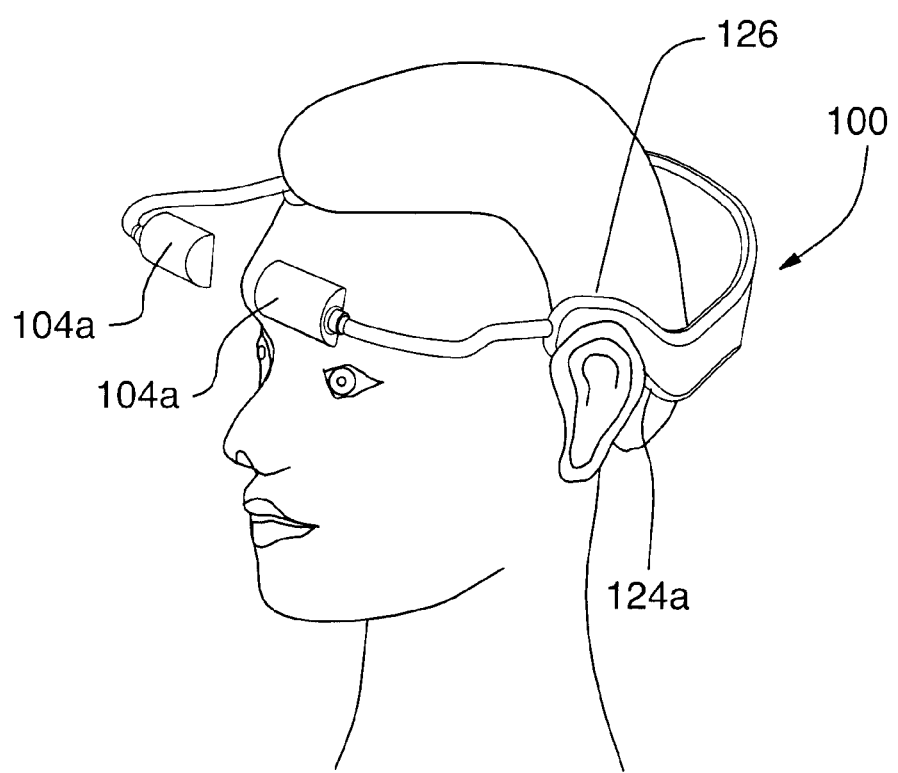
FIG. 2 is a front left perspective view of the artificial light system according to another embodiment of the present invention, positioned on the head of a user.

The portable light system 100 has the general configuration of a circlet or headset and is designed to fit around a user's head, as best shown in FIG. 2. As illustrated in FIGS. 3 and 4, the system 100 comprises a seating portion 102 for seating the system on the user's head, a controller (not shown) and a power source (not shown), such as a battery pack, housed in the seating 102. The portable system further comprises two light pods or panels 104a, 104b, attached to the seating 102 by flexible tubes 106a, 106b, respectively, as best described below.

The seating portion 102 comprises a back portion 108 defining a generally half-circle band surrounding the back portion of the head, generally from one ear to the other, and comprises left and right open ends 110a, 110b adjacent to the right and left ear, respectively, when the system 100 is worn, a lower convex edge 112 and an upper convex edge 114. The back portion 108 further comprises an inner face 116 adjacent to the user's head when the system is worn and an outer face 118. Together, the edges 112 and 114 and the faces 116 and 118 define a generally hollow casing for holding the micro-controller and the batteries. A person skilled in the art will acknowledge that the size and shape of the batteries and controller are adapted to fit within the back portion 108. The back portion is preferably made from a flexible or semi-flexible material such as flexible plastic or rubber-like material, so as to provide enhanced comfort and adjustment.

The seating portion 102 further comprises right and left ear portions 120a, 120b. The ear portions 120a, 120b being mirror images of one another, only right ear portion 120a will be described. A person skilled in the art will understand that a similar description applies to ear portion 120b.

The ear portion 120a generally comprises a back open end 121a connected to the right end 110a of the back portion 108, a front open end 122a, a lower, concave, edge 124a and an upper convex edge 126a. The ear portion 120a further comprises an interior face 128a, adjacent to the users head when the system 100 is worn and a spaced apart exterior face 130a, away from the user's head when the system 100 is worn. Together, the lower edge 124a, the upper edge 126a and the faces 128a and 130a define a hollow structure to accommodate wiring (not shown) for connecting the controller and the batteries to the light pod 104a, as described below. As best shown in FIG. 2, the concave lower edge 124a is designed to fit the contour of the user's ear for enhanced comfort and stability. In one embodiment, the ear portions 112a, 112b are made from the same material than the back portion 108 and form an integral structure therewith.

Now returning to FIGS. 2 and 3, the flexible tubes 106a, 106b will now be described. Again, since flexible tubes 106a and 106b are mirror images of one another, only flexible tube 106a will be described, while it will be acknowledged that a similar description applies to flexible tube 106b. Flexible tube 106a comprises a first, open back end 132a, adjoining the front end 122a of the ear portion 112a to mount the flexible tube 106a to the ear portion 112a, a front open end 134a and a generally elongated, cylindrical wall 136a.

The light pod 104a has a generally half-cylindrical shape and comprises a right end 137a adjoining the front end 134a of the tube 106a and connected thereto, a spaced-apart left end 138a, a curved face 140a and a generally flat face 142a, both faces 140a, 142a extending between the right and left ends 137a, 138a. When the system 100 is positioned on the user's head, the flat face 142a is directed toward the eyes of the user while the curved face 140a is directed away (as seen FIG. 2).

The light pod 104a further comprise four (4) tricolour LED assemblies 144a, 146a, 148a and 150a mounted in a horizontal row on the flat face 142a and directed towards the eyes of the user when the system 100 is worn. In this embodiment, each tricolour LED assembly 144a, 146a, 148a and 150a contains a red LED (612-640 nm), a green LED (510-525 nm) and a blue LED (460-480 nm), housed in a single epoxy package of appropriate size to define somewhat of a miniature bulb. While in this embodiment the pod 104a comprises 4 tricolour LED assemblies 144a, 146a, 148a and 150a, a person skilled in the art will acknowledge that the number and position of the LED assemblies can vary Further, the tricolour LED assemblies 144a, 146a, 148a and 150a could be replaced by individual red, blue and green LEDs.

The tricolour LED assemblies 144a, 146a, 148 and 150a are electrically connected to the battery pack (not shown) and the controller (not shown) via wires, where the red, green and blue LEDs of each assembly 144a, 146a, 148 and 150a are connected to the battery pack and the controller so as to be controlled independently. The wires run from the pod 104a to the battery pack and the controller through the flexible tube 106a, the ear portion 112a and the back portion 108 of the system 100. Similarly to system 20, the controller (not shown) controls the tricolour LED assemblies 144a to 150a to provide pulses of blue light and continuous or pulsed red light, where light parameters can be adjusted as described above. Further, the controller (not shown) may control the tricolour light assemblies 144a to 150a to provide a third light or green light (peak 510-525 nm), which could be pulsed in synchrony with the pulses of bleu light and collaborate therewith to activate melanopsins.

Figure 5:
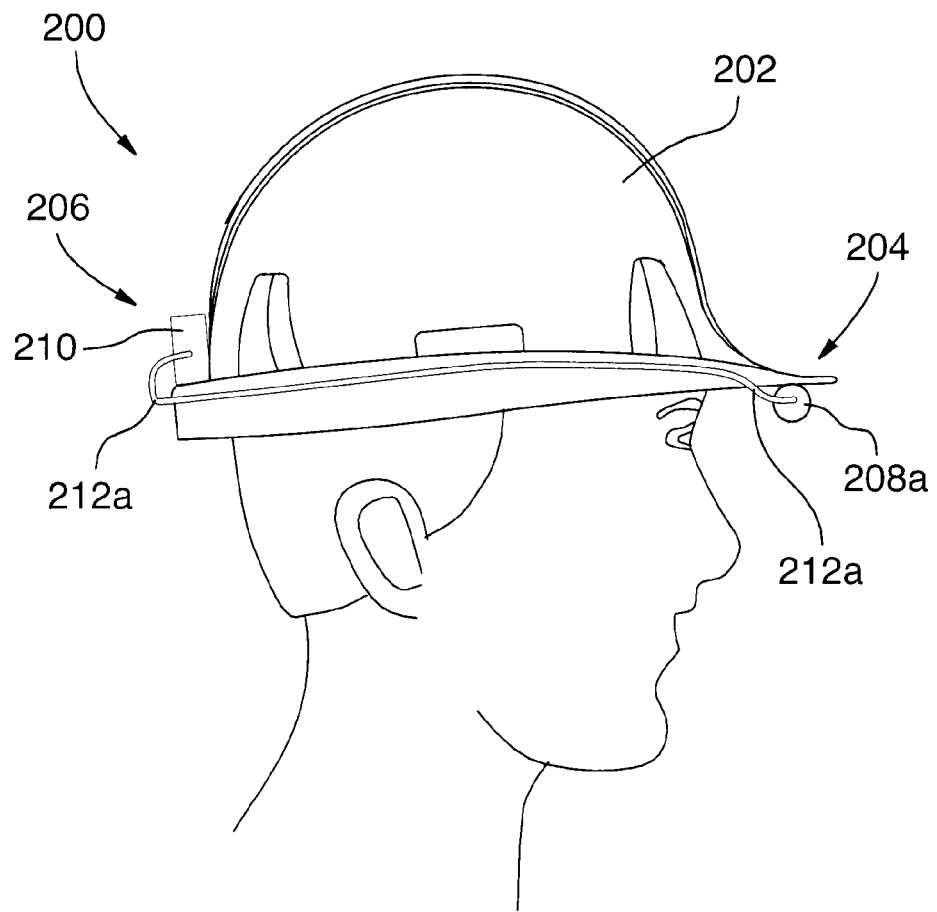
FIG. 5 is a left elevation view of an artificial light system according to a further embodiment of the present invention, showing the security helmet positioned on the head of a user.
Figure 6:
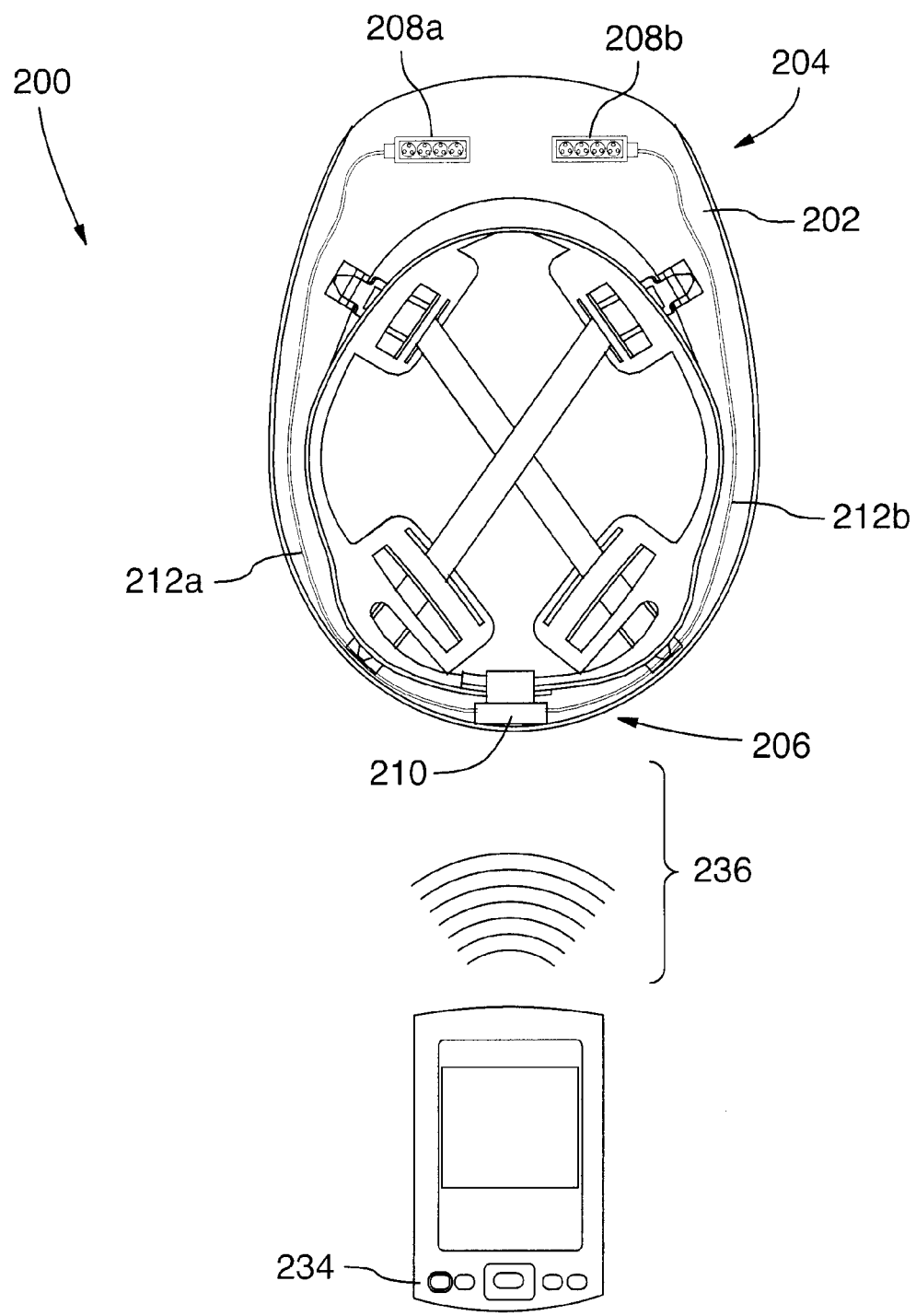
FIG. 6 is a bottom schematic representation of the artificial light system shown in FIG. 5.
Figure 7:
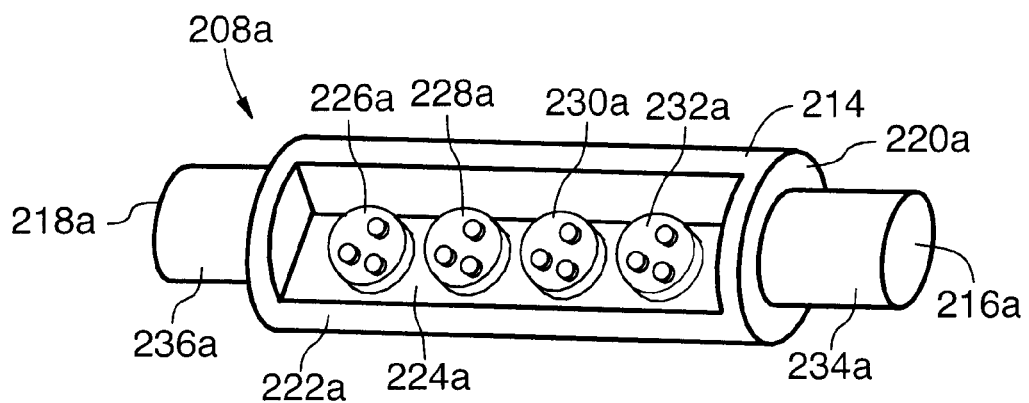
FIG. 7 is an enlarged view of one light pod of the system shown in FIG. 5.

Now referring to FIGS. 5 and 6, a light system 200 according to a further alternate embodiment is shown. In this embodiment, the system 200 is designed to be mounted on a security helmet 202 having a front end 204 and a back end 206. More specifically, the system 200 comprises a pair of light panels or pods 208a, 208b removably mounted under the front end 204 of the helmet with hook-and-loop fasteners such as Velcro™. A person skilled in the art will acknowledge that light pods 208a and 208b could be glued to helmet 202 or mounted by any appropriate way, either permanently or temporarily.

The system 200 further comprises a battery pack comprising rechargeable batteries (e.g. "AA" type batteries or lithium batteries) (not shown) and a controller (not shown) housed in a casing 210 and mounted to the back end 206 of the helmet 202. Similarly to light pods 208a, 208b, the casing 210 can be mounted to the helmet with hook-and-loop fastener or any other permanent or temporary fasteners.

The battery pack and the controller are electrically connected to the light pods 208a, 208b through wires 212a, 212b. The light pods 208a, 208b being identical, only light pod 208a will be described, despite it will be understood that a similar description applies to light pod 208b.

As best shown in FIG. 6, the light pod 208a comprises a generally elongated housing 214a having a first, right end 216a, a second, left end 218a and a curved face 220a extending between the right and left ends 216a, 218a and defining a generally oblong cross-section. On the curved face 220a is defined a generally rectangular recess 222a extending substantially between the right and left ends 216a, 218a on one side of the right pod 208a. The recess 222a comprises a flat face 224a, on which are supported four tricolour LED assemblies 226a, 228a, 230a and 232a, as it will be appreciated below. From each end 216a, 218a of the housing 214a is extending one extension member 234a, 236a having an oblong cross-section similar to that of housing 214, but with a reduced scale.

The four tricolour LED assemblies 226a, 228a, 230a and 232a are similar to tricolour LED assemblies 144a, 146a, 148a and 150a of the system 100 and are mounted in alignment on the flat face 224a of the recess 222a. Each tricolour LED assembly 226a, 228a, 230a and 232a comprises a blue LED (peak 460-480 nm) 226a, a red LED (peak 612-640 nm) 228a, a green LED (peak 510-525 nm) 230a housed in a single epoxy package of appropriate size to define somewhat of a miniature bulb, each LED red, blue and green LED being independently connected to the controller and the battery pack via the wire 212a. The light pod 208a may further comprise a diffuser for diffusions the light emitted by the LEDs 226a-232a.

As shown in FIG. 5, the light pods 208a, 208b are mounted under the front end 204 of the security helmet 202 such that the light beams provided by the tricolour LED assemblies 226a-232a from each light pod 208a, 208b is directed towards one eye of a user, when the helmet is worn. In one embodiment of the present invention, the tricolour LED assemblies 226a-232a have a divergence angle of 120°.

The controller of the system 200 is programmed to modulate the parameters of the light emitted by the tricolour LED assemblies 226a-232s, such as the light intensity, pulse frequency, the duration of light emission/interruption within a cycle and the duration of the light treatment, as described above in relation with the system 20.

The system 200 also comprises a hand held computer 234, such as a Palm EZ™, and communication means 236 allowing electronic communication between the handheld computer 234 and the controller, such as an Infrared communication device. The communication means 236 enables modification of the controller's program to update or reset the parameters of light conditions. It will be understood that the handheld computer could be replaced by a laptop computer or a desktop computer and communication between the controller and the computer could be achieved with cables or the like, instead of the Infrared device.

While the light system of the present invention has been described with reference to the light systems 20, 100 and 200, a person skilled in the art will appreciate that numerous light system configurations would be possible. For instance, the light system could be configured to be installed in a means of transport such as an aircraft, a car, a bus, a boat or the like. In such an embodiment, the light system could comprise a housing in which are mounted a light source, a controller and batteries. The housing could be provided with mounting members such as brackets, supports or adhesives for mounting the light system to a portion of the vehicle and directing the light emitted by the light source towards the eyes of a user while avoiding blinding the driver of the vehicle. For instance, such a portable light system could be mounted to the dashboard of a car or of a truck to enhance vigilance of an individual driving the same at night.

Alternatively, the light system of the present invention could be adapted to fulfill the needs of the entertainment industry, where lengthening customers vigilance and awakening is desirable. For instance, the light system could be configured to be installed in casinos, proximal to game tables, slot machines and the like or, in a larger scale, in arenas, nightclubs and other social establishments. Alternatively, the light system of the present invention could be used to synchronize the biological clock of athletes, astronauts, military and civil aircraft pilots that are required to perform highly demanding tasks. In such cases, the light system of the present invention could be used to synchronize the maximal awakening, performance and vigilance period of the biological clock with the task to be performed. For instance, where an athlete typically reaches maximum performances around 10:00 am and has a competition scheduled at 7:00 pm on a later day, the light system may be used to synchronize the biological clock so that the athlete system will be at his peak of performance during the competition.

Further, it will be appreciated that the light system of the present invention may find use with human subjects, as well as with any other type of subjects having circadian rhythms or conditions responding to light conditions. For instance, the light system of the present invention may be useful for influencing circadian rhythms of generally nocturne animals living in zoos, pet shops and the like to modify their biological clock to therefore provide customers with the opportunity to observe activities of such generally nocturne animals during operation hours.

As such, the period of time for which the subjects are submitted to light may vary to attain the desired effects. According to one embodiment, the period of time is predetermined and preset prior to subjecting the subject to the light conditions. According to one embodiment, the predetermined period ranges from about 5 minutes to about 18 hours, and preferably from about 1 hour to about 8 hours, and more preferably from about 3 hours to about 5 hours.

Having described various configurations of the light system of the present invention, a method for influencing a condition in a subject with the light system 20 will now be described by way of examples.

Example 1

Circadian rhythms in body temperature, heart beat and arterial pressure have been demonstrated. Body temperature has been reported to influence human performance, vigilance and alertness, which are reported to be better when body temperature is high and inferior when body temperature is low.

Material and Method
Subject—
The experiments were conducted on a 40-year old Caucasian male. The subject was generally healthy and did not report health condition generally associated with circadian rhythms disorders. The subject also maintained a regular sleep schedule over the two weeks of evaluation.

Light Exposure—
Twenty (20) minutes prior to each experiment, two (2) drops of tropicamide 1% (Mydriacyl®) were applied in each eye of the subject, to fully dilate pupils and avoid variation of pupils dilatation during experiments. The subject was comfortably seated in a reclining chair for the total duration of each experiment. Light stimulations were administered with a ganzfeld (Color Dome; Espion system, DIAGNOSYS LLC, Lowell, Mass.), following the manufacturer specifications.

Each experiment was conducted over a four-hour period, in which light conditions were applied for a two-hour period and more specifically between 12:30 am and 2:30 am. The parameters of each light condition are summarized in Table 1 below. The first week of experimentation was conducted under very dim light to avoid any melatonin suppression, to simulate and monitor the secretion of melatonin by the participant in absence of light. This experiment was further used as control to evaluate the effect of the light conditions tested during weeks 2 and 3.

TABLE 1

Parameters of light conditions

| | Week 1 (Control) | Week 2 | Week 3 |
|---|---|---|---|
| Duration of tests (hours) (From 11:00 pm to 3:00 am) Blue light (peak 470 nm) | 4 | 4 | 4 |
| Total exposure to light conditions (hours) (From 12:30 am to 2:30 am) | 2 | 2 | 2 |
| Frequency (Hz) (ms) | No Light | 58.82 (17 ms) | continuous |
| Duration of light pulse (ms) | n/a | 4 ms | continuous |
| Duration of Interruption (ms) | n/a | 13 ms | n/a |
| Light intensity ($\mu W/cm^2$) | n/a | 40.2 | 40.2 |

Temperature Measurements—
In each experiment, body temperature was assessed every 15 minutes, between 11:00 pm and 3:00 am. Body temperature was measured with a ThermoScan™ ear thermometer (Braun GmbH, Frankfurter, Germany).

Figure 8:
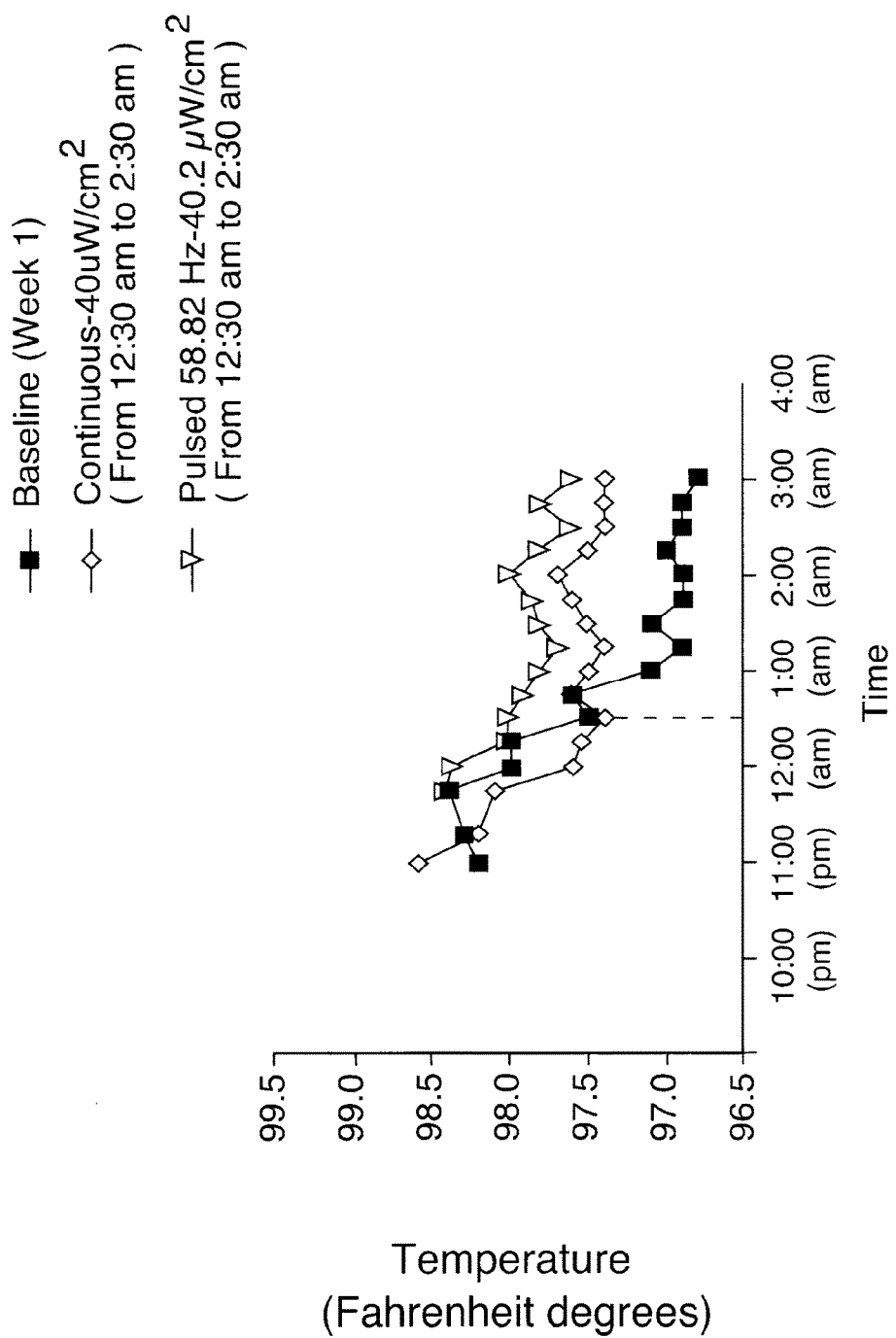
FIG. 8 is a graph illustrating the effect of an exposure to pulsed blue light on body temperature, according to one embodiment of the present invention.

Results
Results of the experiments are shown in FIG. 8. These results indicates that both the continuous and pulsed blue light are effective in increasing the body temperature but that the pulsed blue light (58.82 Hz) is more efficient than the continuous light, for a same intensity (40.2 $\mu W/cm^2$).

Example 2

Melatonin is a good marker of the SCN response to light since suppression of melatonin secretion is correlated to the response of SCN to light stimuli. Accordingly, a strong suppression of melatonin secretion is an indicator of a strong response of SCN to a light stimulus. Further, because melatonin is secreted in saliva and can be monitored relatively easily by ELISA, the use of this hormone as indicator of SCN activity is convenient.

In this example, four (4) different light conditions were tested on a same subject over 4 weeks, each experiment being spaced from one another by one week, to assess the effect of such light conditions on melatonin secretion.

Material and Method

Subject—

The experiments were conducted on a 60-year old Caucasian male. The subject was generally healthy and did not report health condition generally associated with circadian rhythms disorders. The subject also maintained a regular sleep schedule over the four weeks of evaluation.

Light Exposure—

Twenty (20) minutes prior to each experiment, two (2) drops of tropicamide 1% (Mydriacyl®) were applied in each eye of the subject, to fully dilate pupils and avoid variation of pupils' dilatation during experiments. The subject was comfortably seated in a reclining chair for the total duration of each experiment. Light stimulations were administered with a ganzfeld (Color Dome; Espion system, DIAGNOSYS LLC, Lowell, Mass.), following the manufacturer specifications.

Each experiment was conducted over a three-hour period, in which light conditions were applied for a two-hour period, and more specifically between 12:30 am and 2:30 am. The parameters of each light condition are summarized in Table 2 below. The first week of experimentation was conducted in absence of light, to monitor the secretion of melatonin by the participant under very dim light in order to avoid any melatonin suppression. This experiment was further used as control to evaluate the effect of the light conditions tested during weeks 2 to 4.

TABLE 2

Parameters of light conditions

|  | Week 1 (Control) | Week 2 | Week 3 | Week 4 |
|---|---|---|---|---|
| Duration of tests (hours) (From midnight to 3:00 am) | 3 | 3 | 3 | 3 |
| Blue light (peak 470 nm) | | | | |
| Total exposure to light conditions (hours) (From 12:30 am to 3 am) | 2 | 2 | 2 | 2 |
| Frequency (Hz) (ms) | No Light | 58.82 (17 ms) | 100 (10 ms) | continuous |
| Duration of light pulse (ms) | n/a | 4 ms | 4 ms | continuous |
| Duration of Interruption (ms) | n/a | 13 ms | 6 ms | n/a |
| Light intensity (μW/cm$^2$) | n/a | 40.2 | 70 | 40.2 |
| Red light (640 nm) | | | | |
| Total exposure to light conditions (hours) | 2 | 2 | 2 | 2 |
| Frequency (Hz) | n/a | continuous | continuous | 58.2 |
| Duration of light pulses (ms) | n/a | n/a | n/a | 4 |
| Duration of interruption (ms) | n/a | n/a | n/a | 13 |
| Light intensity (μW/cm$^2$) | n/a | 9.25 | 9.25 | 7.6 |

Melatonin Measurements—

In each experiment, saliva samples were collected with salivettes (Sarstedt Inc., Newton, N.C.) at midnight, 1:00 am, 1:15 am, 1:30 am, 1:45 am, 2:00 am, 2:30 am and 3:00 am. Each saliva sample was frozen immediately after collection and melatonin concentration was determined using the Direct Saliva Melatonin ELISA immunoassay commercialised by American Laboratory Products Company (ALPCO Diagnosis, Salem, N.H., U.S.A).

Results

Figure 9:
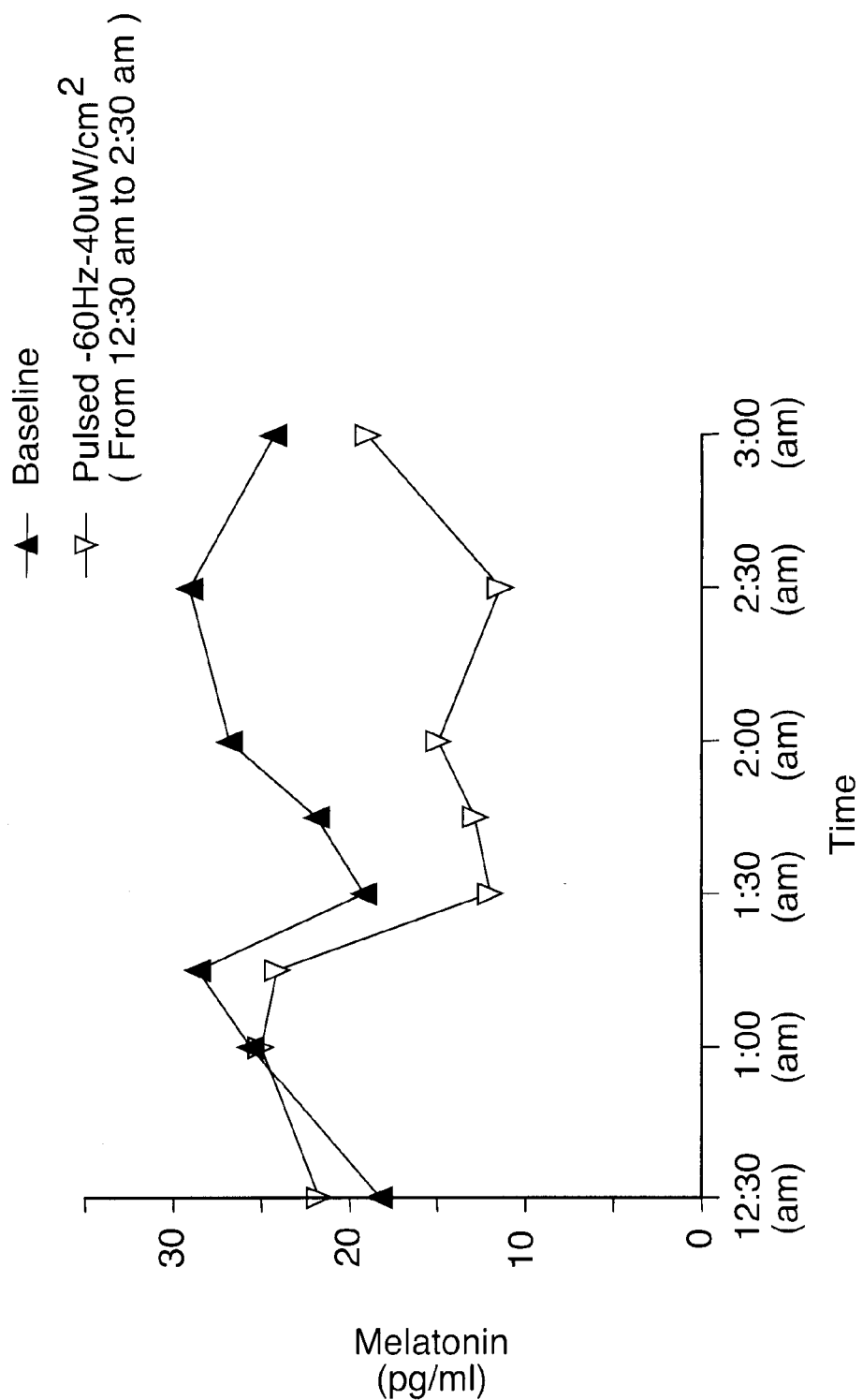
FIG. 9 is a graph illustrating the effect of a light exposure on melatonin secretion according to another embodiment of the present invention.
Figure 10:
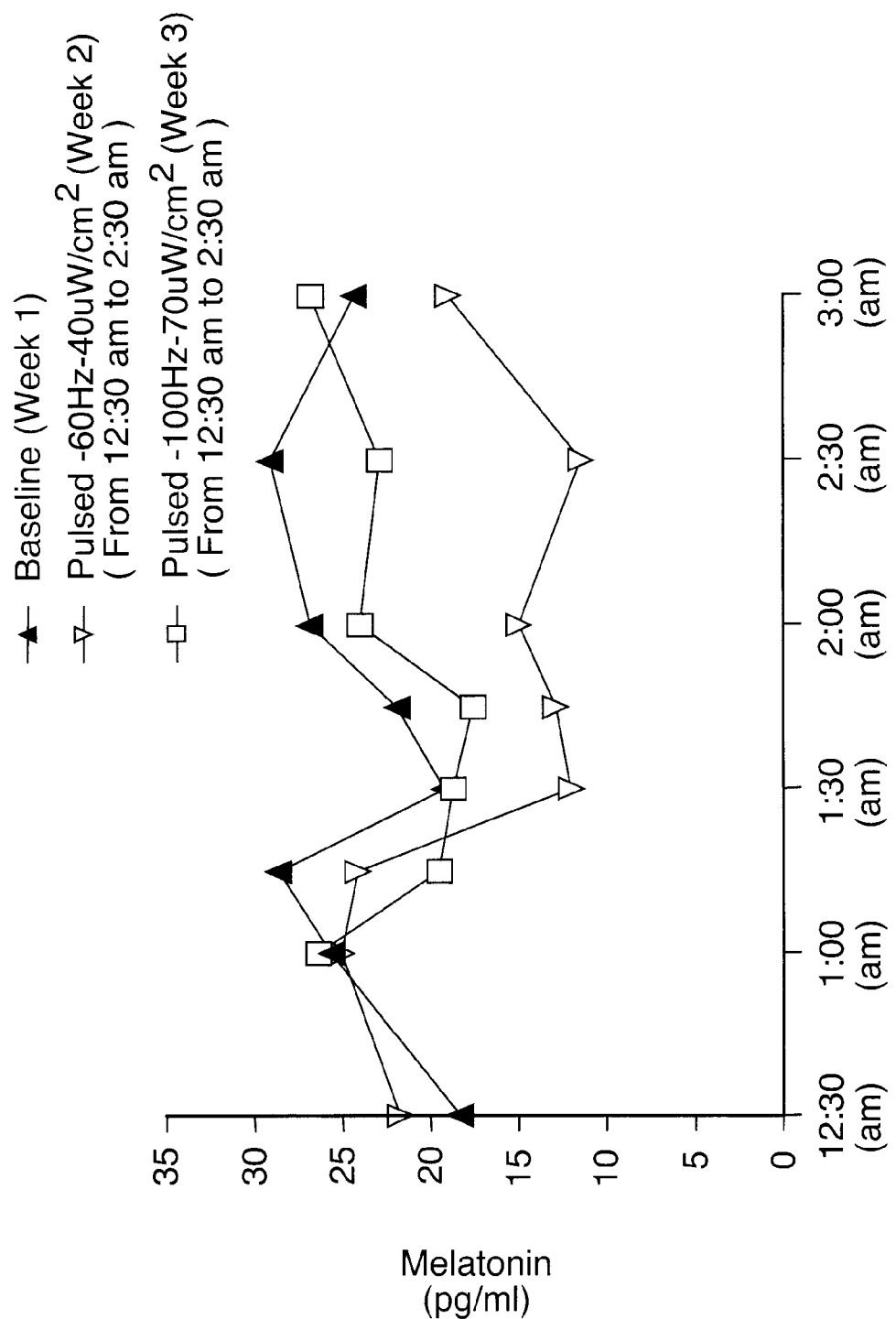
FIG. 10 is a graph illustrating the effect of a light exposure on melatonin secretion according to yet another embodiment of the present invention.
Figure 11:
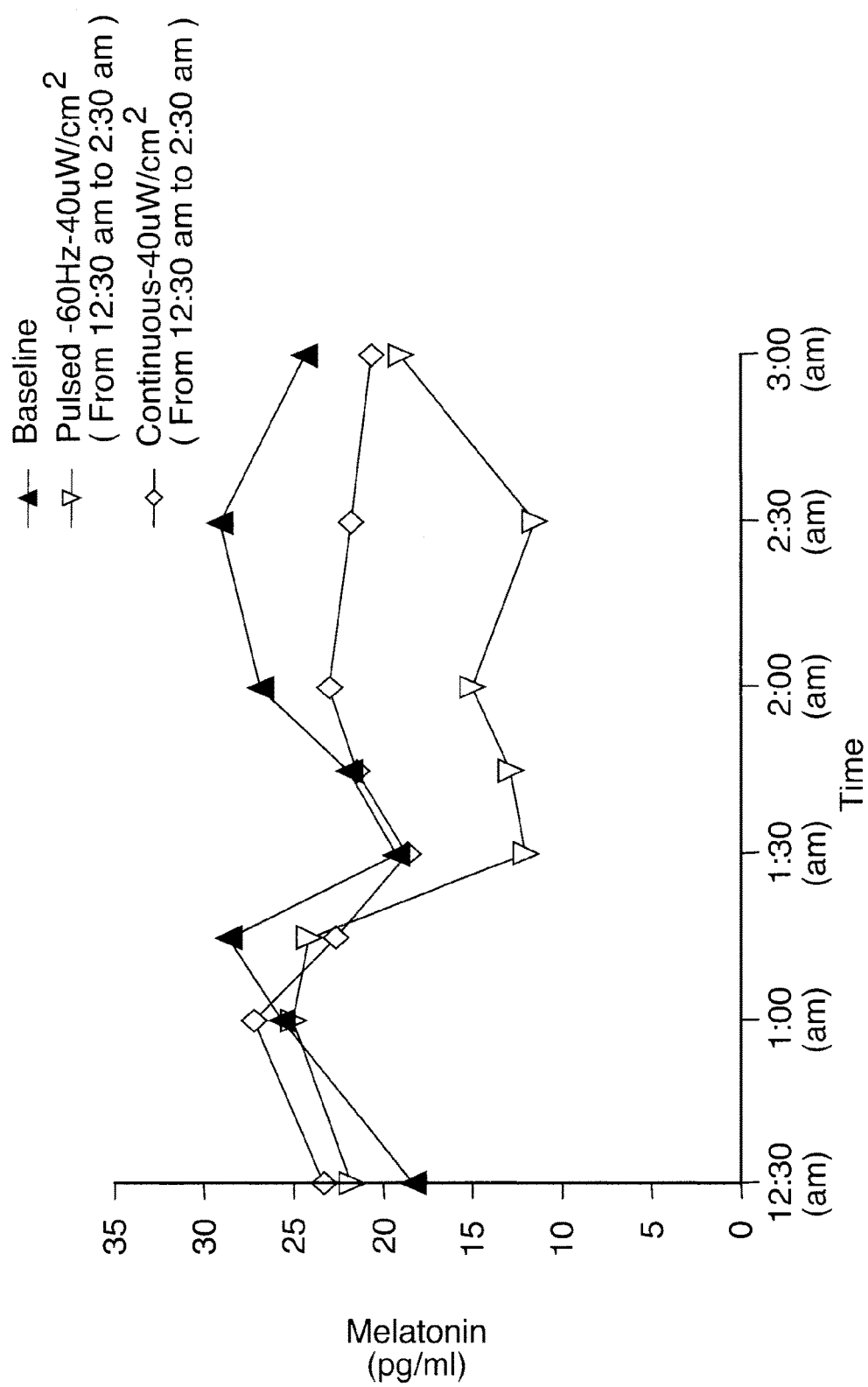
FIG. 11 is a graph illustrating the effect of a light exposure on melatonin secretion according to a further embodiment of the present invention.

Results of the experiments are summarized in Tables 3 and 4, as well as in FIGS. 9 to 11.

TABLE 3

Melatonin secretion level, expressed in pg/ml.

|  | Week 1 (Control) | Week 2 | Week 3 | Week 4 |
|---|---|---|---|---|
| Midnight |  | 19.60 |  | 23.31 |
| 1:00 am | 25.63 | 25.07 | 26.42 | 22.67 |
| 1:15 am | 28.61 | 24.16 | 19.50 | 18.65 |
| 1:30 am | 19.23 | 12.02 | 18.70 | 21.47 |
| 1:45 am | 21.91 | 12.88 | 17.60 | 22.99 |
| 2:00 am | 26.84 | 14.98 | 24.05 | 21.76 |
| 2:30 am | 29.08 | 11.45 | 22.90 | 20.63 |
| 3:00 am | 24.34 | 18.99 | 26.80 | 19.60 |

TABLE 4

Difference of secretion level by comparison with control level (week 1), expressed in percent (%), where "↓" and "↑" indicate a decrease and an increase in melatonin secretion, respectively.

|  | Week 2 | Week 3 | Week 4 |
|---|---|---|---|
| Midnight |  |  |  |
| 1:00 am | ↓2.2 | ↑3.1 | ↓11.5 |
| 1:15 am | ↓15.6 | ↓31.8 | ↓34.8 |
| 1:30 am | ↓37.5 | ↓2.8 | ↑11.6 |
| 1:45 am | ↓41.2 | ↓19.7 | ↑4.9 |
| 2:00 am | ↓44.2 | ↓10.4 | ↓18.9 |
| 2:30 am | ↓60.6 | ↓21.3 | ↓29.1 |
| 3:00 am | ↓22 | ↑10.1 | ↓19.3 |

As best shown in FIG. 9, results of these experiments show that a 2-hour exposure to pulsed blue light (i.e. wavelength peak at 470 nm) and continuous red light (i.e. wavelength peak at 640 nm), where blue light has an intensity of 40 μW/cm$^2$ and a frequency of 58.82 Hz (4 ms light on/13 ms light off), significantly contributes to reduce melatonin secretion, where melatonin secretion appears to be roughly 40% lower under light exposure (week 2) by comparison with the control (week 1).

Now turning to FIG. 10, results show that a 2-hour exposure to pulsed blue light (wavelength peak at 470 nm) and continuous red light (wavelength peak at 640 nm), where blue light has an intensity of 70 vW/cm$^2$ and a frequency of 100 Hz (4 ms light on/6 ms light off), also contributes to reduce melatonin secretions, with a decrease that averages 24% when compared to the no light condition. Similar results were achieved with continuous blue light (470 nm) at 40 μW/cm$^2$, with about 19% suppression when compared with no light exposure (week 1), as best shown in FIG. 11. Results shown in FIGS. 10 and 11 tend to demonstrate that the use of pulsed blue light in the presence of red light is twice as more efficient as continuous blue light. Because light is pulsed, it is more effective (twice as much when compared to continuous blue light) and it becomes possible to reduce the intensity or the total duration of light exposure without compromising it effect on the biological clock. Under such light conditions, blue light hazard are minimized without reducing the efficacy of exposure to blue light on melatonin secretion.

FIGS. 9 to 11 also tend to support that with a same subject, a lower frequency of blue light cycles (e.g. 58.82 Hz) can be more efficient than a higher frequency (e.g. 100 Hz) or continuous blue light, even if under the later conditions the light intensity is increased by 57%.

No stroboscopic effect was noted and no discomfort related thereto was reported by the subject of the experiment upon testing of the exemplary conditions.

Example 3

To assess the efficacy of the light system of the present invention, a light system generally corresponding to the light system 200 was tested by night-shift workers of a saw mill based in the province of Québec, Canada.

Material and Method

Subjects—

The experiments were conducted over three (3) weeks (i.e. week 1 to week 3) in a saw mill based in the province of Quebec, Canada. One different team of graders was assigned to the night shift for each of the three experiment weeks, where each team comprised 4 graders. For each team of workers, the graders were distributed into two (2) experimental groups, namely two (2) graders in the Control Group and two (2) graders in the Subject Group. As such, the experiments were conducted on a total of six (6) different graders of the Control Group and six (6) different graders of the Subject Group. The graders were generally healthy and did not report health condition generally associated with circadian rhythms disorders.

The graders of the Subject Group were provided with a light system similar to the light system 200, integrated to a security helmet, prior to conducting the experiments. The graders of the Subject Group were provided with instructions as to how the light system had be positioned and operated throughout the experiments, as well as to how the assessment of the light system had to be conducted. The results of the experiments conducted on the graders of the Subject Group were compared to those of 6 graders of the Control Group. Graders of the Control Group performed their work without the light system.

During the course of the experiments, one grader of the Subject Group did not attend work on multiple occasions. As such, data obtained for this grader were discarded. For preserving an equal number of graders within both the Control Group and the Subject Group, the data obtained for one random grader of the Control Group were discarded. Therefore, data were compiled for a total of five (5) graders of the Control Group and five (5) workers of the Subject Group.

Light Exposure—

The security helmet comprising the light system had to be worn by each subject, and the light system operated, from midnight to 5:00 am. From 5:00 am until 8:00 am, the light system had to be turned off. The parameters of the light exposure are summarized in Table 5 below. In this experiment, the blue and red lights were desynchronized. More specifically, when the blue light was on, the red light was off. Conversely, when the blue light was off, the red light was on.

TABLE 5

Parameters of light conditions

| | Control Group | Subject Group |
|---|---|---|
| Duration of tests (hours) (From midnight to 5:00 am) | 5 | 5 |
| Blue light (peak 470 nm) | | |
| Total exposure to light conditions (hours) (From 12:30 am to 3 am) | No Light | 5 |
| Frequency (Hz) (ms) | n/a | 70 (14 ms) |
| Duration of light pulse (ms) | n/a | 4 ms |
| Duration of Interruption (ms) | n/a | 10 ms |
| Light intensity (µW/cm$^2$) | n/a | 30 |
| Red light (640 nm) | | |
| Total exposure to light conditions (hours) | n/a | 2 |
| Frequency (Hz) (ms) | n/a | 70 (14 ms) |
| Duration of light pulses (ms) | n/a | 10 |
| Duration of interruption (ms) | n/a | 4 |
| Light intensity (µW/cm$^2$) | n/a | 10 |

Productivity Measurement—

The productivity of the graders from each of the Control Group and the Subject Group was assessed individually based on the weekly means of revenues generated by each worker in relation to graded Thousand Board Feet ($/Graded TBF). The data for both the Control Group and the Subject Group were averaged. The averaged data for the Subject Group were then compared to those of the Control Group.

Results

During the three weeks where the experiments were conducted, the averaged productivity of the control workers was 279.2 $/Graded TBF. During the same three weeks, the averaged productivity of the subject workers was 283.8 $/Graded TBF. In other words, the productivity of the workers provided with the light system of the present invention was increase by 4.6 $/Graded TBF.

As response to light is dependant upon age, ethnicity and sex, a person skilled in the art will understand that optimal light conditions may vary significantly amongst individuals and that the exemplary conditions described in the above examples could be set and adapted differently for each subject.

Although the foregoing description and accompanying drawings relate to specific preferred embodiments of the present invention as presently contemplated by the inventor, it will be understood that various changes, modifications and adaptations, may be made.

The invention claimed is:

1. A method for stimulating the activity of the suprachiasmatic nuclei in a subject, the method comprising:
    providing a first light-emitting source apt to generate a first light having optical parameters known to stimulate an increase in the activity of the suprachiasmatic nuclei of the subject upon eye exposure in continuous emission conditions, said optical parameters including a first spectrum comprised between 420 nm and 540 nm;
    generating the first light using said first light-emitting source in a pulsed regime at a pulsing frequency within a frequency range of about 60 Hz to about 70 Hz; and
    exposing the eyes of the subject to the generated pulsed first light;

wherein said frequency range is selected such that:
- a perception of a stroboscopic effect within said first light by the subject upon said exposing is substantially avoided; and
- the stimulation of an increase in the activity of the suprachiasmatic nuclei in the subject resulting from said exposing is about twice as effective as under said continuous emission conditions.

2. The method according to claim 1, wherein the first light has a first intensity of at least about 5 µW/cm².

3. The method according to claim 1, wherein said optical parameters of the first light include a first wavelength peak between 446 nm and 483 nm.

4. The method according to claim 1, wherein said pulsing frequency is about 60 Hz.

5. The method according to claim 1, wherein said pulsing frequency is about 70 Hz.

6. The method according to claim 1, wherein the exposing of the eye of the subject to the first light is performed for a total exposure period ranging from about 5 minutes to about 18 hours.

7. The method according to claim 1, wherein the first light defines a train of light pulses each having a light emission duration between 1 and 10 ms and separated by light interruptions having a light interruption duration between 4 and 16 ms.

8. The method according to claim 7, wherein the light emission duration is about 4 ms.

9. The method according to claim 8, wherein the light interruption duration is about 13 ms.

10. The method according to claim 1, further comprising:
- providing a second light-emitting source apt to generate a second light having a second spectrum comprised between 590 nm and 650 nm;
- generating the second light using said second light-emitting source and exposing the eyes of the subject to the generated second light during a same exposure period as the exposing the eyes of the subject to the generated pulsed first light.

11. The method according to claim 10, wherein the second light has a second wavelength peak between 612 nm and 640 nm.

12. The method according to claim 10, wherein the second light is emitted continuously.

13. The method according to claim 10, further comprising pulsing the second light.

14. The method according to claim 13, wherein:
- the first light and second light each define a train of light pulses each having a light emission duration between 1 and 10 ms and separated by light interruptions having a light interruption duration between 4 and 16 ms; and
- the second light is pulsed at the same pulsing frequency as the first light, the pulsing of the second light being desynchronized with the pulsing of the first light such that each light pulse of the second light is emitted during a light interruption of the first light.

15. A system to generate light for stimulating the activity of the suprachiasmatic nuclei in a subject upon exposing the eyes of the subject to said light, the system comprising:
- a first light-emitting source apt to generate a first light having optical parameters known to stimulate an increase in the activity of the suprachiasmatic nuclei of the subject upon eye exposure in continuous emission conditions, said optical parameters including a first spectrum comprised between 420 nm and 540 nm;
- a controller operatively coupled to the first light-emitting source, the controller being configured to control said first light-emitting source to generate the first light in a pulsed regime at a pulsing frequency within a frequency range of about 60 Hz to about 70 Hz, wherein said frequency range is selected such that:
  - a perception of a stroboscopic effect within said first light by the subject upon said exposing is substantially avoided; and
  - the stimulation of an increase in the activity of the suprachiasmatic nuclei in the subject resulting from said exposing is about twice as effective as under said continuous emission conditions.

16. The system according to claim 15, wherein the first light has a first intensity of at least about 5 µW/cm².

17. The system according to claim 15, wherein said optical parameters of the first light include a first wavelength peak between 446 nm and 483 nm.

18. The system according to claim 15, wherein said pulsing frequency is about 60 Hz.

19. The system according to claim 15, wherein said pulsing frequency is about 70 Hz.

20. The system according to claim 15, wherein the first light defines a train of light pulses each having a light emission duration between 1 and 10 ms and separated by light interruptions having a light interruption duration between 4 and 16 ms.

21. The system according to claim 20, wherein the light emission duration is about 4 ms.

22. The system according to claim 21, wherein the light interruption duration is about 13 ms.

23. The system according to claim 15, further comprising:
- a second light-emitting source apt to generate a second light having a second spectrum comprised between 590 nm and 650 nm;
wherein the controller is operatively coupled to the second light-emitting source, the controller being further configured to control said second light-emitting source to generate the second light during a same exposure period as the pulsed first light.

24. The system according to claim 23, wherein the second light has a second wavelength peak between 612 nm and 640 nm.

25. The system according to claim 23, wherein the controller is configured to control the second light-emitting source to emit the second light continuously.

26. The method according to claim 23, wherein the controller is configured to control the second light-emitting source to generate the second light in a pulsed regime.

27. The method according to claim 26, wherein:
- the first light and second light each define a train of light pulses each having a light emission duration between 1 and 10 ms and separated by light interruptions having a light interruption duration between 4 and 16 ms; and
- the second light is pulsed at the same pulsing frequency as the first light, the pulsing of the second light being desynchronized with the pulsing of the first light such that each light pulse of the second light is emitted during a light interruption of the first light.

* * * * *